US006923990B2

(12) United States Patent
Capelli

(10) Patent No.: US 6,923,990 B2
(45) Date of Patent: Aug. 2, 2005

(54) STABILIZED SILVER-ION AMINE COMPLEX COMPOSITIONS AND METHODS

(76) Inventor: Christopher Capelli, 5125 Fifth Ave., Apt. G-1, Pittsburgh, PA (US) 15232

( * ) Notice: Subject to any disclaimer, the term of this patent is extended or adjusted under 35 U.S.C. 154(b) by 86 days.

(21) Appl. No.: 10/421,420

(22) Filed: Apr. 23, 2003

(65) Prior Publication Data

US 2004/0213830 A1 Oct. 28, 2004

(51) Int. Cl.$^7$ .................. A01N 55/02; A01N 59/16; A01N 25/22; A61K 31/28; A61K 33/38
(52) U.S. Cl. .................. 424/618; 424/402; 424/404; 424/409; 424/411; 424/414; 424/422; 424/423; 424/424; 424/425; 424/426; 424/430; 424/443; 424/445; 424/446; 424/447; 424/DIG. 13; 514/495; 514/579; 514/646; 514/663; 514/669; 514/944; 514/945; 514/970; 514/972; 514/973
(58) Field of Search .................. 424/618, 402, 424/404, 409, 411, 414, 422–426, 430, 443, 445, 446, 447, DIG. 13, 400; 514/495, 579, 646, 663, 669, 944, 945, 970, 972, 973

(56) References Cited

U.S. PATENT DOCUMENTS

| | | | |
|---|---|---|---|
| 5,326,567 A | | 7/1994 | Capelli ................ 424/405 |
| 5,429,819 A | * | 7/1995 | Oka et al. ............ 424/400 |
| 5,510,109 A | | 4/1996 | Tomioka et al. ...... 424/421 |
| 5,510,315 A | * | 4/1996 | Kurotsu et al. ...... 504/115 |
| 6,093,414 A | * | 7/2000 | Capelli ................ 424/405 |
| 6,197,214 B1 | * | 3/2001 | Virnig et al. .......... 252/184 |
| 6,468,521 B1 | * | 10/2002 | Pedersen et al. ...... 424/78.17 |

OTHER PUBLICATIONS

Derwent abstract 1991–105683, abstracting JP 3–47101 (1991).*

* cited by examiner

*Primary Examiner*—John Pak
(74) *Attorney, Agent, or Firm*—Medlen & Carroll, LLP

(57) ABSTRACT

The present invention relates to new silver-ion super-complex compositions. More particularly, the present invention describes silver-ion super-complex compositions comprising a silver-thiosulfate ion complex further complex with a primary, secondary or tertiary amine. These silver-ion super-complex compositions are stable in a saline environment and have improved solvent miscibility.

26 Claims, No Drawings

STABILIZED SILVER-ION AMINE COMPLEX COMPOSITIONS AND METHODS

FIELD OF INVENTION

The present invention relates to silver ion compositions and processes for making such compositions effective as antibacterial, antiviral and/or antifungal agents. In one embodiment, the invention relates to a method of producing silver thiosulfate ion compositions and coating medical devices comprising such compositions. In a preferred embodiment, the present invention relates to carrier-free aqueous silver thiosulfate complexes stabilized by amines.

BACKGROUND

Topical antimicrobials are currently prescribed by healthcare providers to prevent and treat a variety of serious skin infections such as impetigo, infected diabetic ulcers, venous stasis ulcers, infected surgical wounds, burns, acne, psoriasis and other topical infections. Increasingly, topical antimicrobials that contain antibiotics are not effective against microbes which have developed drug resistance (i.e., antibiotic-resistant microbes).

Drug resistance is usually caused by a mutation within the microbe. When a colony of microbes is subjected to a dose of an antimicrobial, most of the bacteria die. However, occasionally some microbes, by chance, harbor mutant genes that render them resistant to the antimicrobial drug. Not only do these bacteria survive the antimicrobial treatment, but they transfer their "drug resistant" genes to their progeny (one bacterium can leave approximately 17,000,000 offspring within 24 hours). As a result, a specific antibiotic or antimicrobial used to treat an infection caused by that microbe may no longer be effective. Furthermore, once a microbe develops resistance to a specific antimicrobial, there is the possibility that the microbe will concomitantly be resistant to the entire class of antimicrobials.

Certain antimicrobials, especially antibiotics, are becoming increasingly ineffective due to the rapid increase in drug-resistant forms of microbes. For example, mupirocin ointment (Bactroban®, SmithKline Beecham) is a topical antimicrobial used most frequently for treatment of impetigo. Mupirocin has been shown to be highly effective against *Staphylococcus aureus, S. epidermidis, S. saprophyticus,* and *Streptococcus pyogenes*. Unfortunately, microbes frequently develop drug resistance to mupirocin.

What is needed are pharmaceutical compositions useful in the prevention and treatment of infections and diseases which comprise an antimicrobial agent and one or more medicinal agents and which remain antimicrobially active in an aqueous environment, and more specifically an aqueous environment that contains sodium chloride.

SUMMARY OF THE INVENTION

The present invention relates to silver ion compositions and processes for making such compositions effective as antibacterial, antiviral and/or antifungal agents. In one embodiment, the invention relates to a method of producing silver thiosulfate ion compositions and coating medical devices comprising such compositions. In a preferred embodiment, the present invention relates to carrier-free aqueous silver thiosulfate complexes stabilized by amines.

One aspect of the present invention contemplates a composition, comprising a silver thiosulfate ion complex in association with an amine. In one embodiment, the amine is selected from the group consisting of primary amines, secondary amines and tertiary amines. In another embodiment, the amine comprises tri-hydroxymethyl aminomethane. In one embodiment, the composition further comprises a medical device, wherein said medical device is impregnated with said composition. In one embodiment, the composition is attached to one or more hydrophilic polymers. In one embodiment, the one or more hydrophilic polymers are part of a wound dressing. In one embodiment, the wound dressing is selected from the group consisting of gauzes, compresses, hydrocolloids, xerogels and foams. In one embodiment, the medical device is configured for placement inside a patient. In one embodiment, the medical device is selected from the group consisiting of implants, sutures and other materials left in a body cavity for a period of time. In another embodiment, the medical device is a catheter. In one embodiment, the catheter is a urinary catheter. In one embodiment, the medical device is selected from the group consisting of an ostomy appliance and an incontinent device.

One aspect of the present invention contemplates, a method, comprising: a) providing; i) a patient exhibiting symptoms of infection; and ii) a composition, comprising a silver thiosulfate ion complex in association with an amine; and b) administering said composition to said patient under conditions such that at least one symptom of said infection is reduced.

One aspect of the present invention contemplates, a method, comprising: a) providing: i) a patient with a wound; and ii) a composition, comprising a silver thiosulfate ion complex in association with an amine; and b) delivering said composition to said wound.

One aspect of the present invention contemplates a method, comprising: a) providing; i) a patient at risk for an infection; and ii) a composition, comprising a silver thiosulfate ion complex in association with an amine; and b) administering said composition to said patient.

One aspect of the present invention contemplates a composition, comprising: a) a silver thiosulfate ion complex; and b) an amine associated with said complex. In one embodiment, said amine is selected from the group consisting of primary, secondary and tertiary. In another embodiment, said amine comprises tri-hydroxymethyl aminomethane. In one embodiment, said composition further comprises a medical device, wherein said medical device is impregnated with said composition. In one embodiment, said medical device comprises one or more hydrophilic polymers. In another embodiment, said medical device is selected from the group consisting of a wound dressing, an ostomy appliance and an incontinence device. In one embodiment, said composition further comprises sulfite or bisulfite ion, wherein said ion preserves said amine.

Another aspect of the present invention, contemplates a method, comprising: a) providing; i) a silver thiosulfate ion complex; and ii) an amine; b) mixing said complex with said amine to produce a stabilized amine silver thiosulfate complex. In one embodiment, said stabilized complex retains stability in a saline environment. In one embodiment, said saline environment comprises sodium and chloride ions. In one embodiment, said stabilized complex is soluble in non-aqueous environments.

Another aspect of the present invention contemplates a method, comprising: a) providing; i) a patient exhibiting a wound; and ii) an amine stabilized silver thiosulfate ion complex; b) contacting said wound with said complex under conditions such that said complex exhibits activity selected from the group consisting of antibacterial, antiviral antifungal and any combination thereof.

Another aspect of the present invention contemplates a method comprising: a) providing; i) a silver thiosulfate ion complex in an aqueous solution, ii) an amine; and iii) a solvent; and b) adding said amine and said solvent to said aqueous solution to create a biphasic separation. In one embodiment, said solvent is acetone.

Another aspect of the present invention contemplates an apparatus comprising; a) a medical device at least partially coated with a composition, said composition comprising i) a carrier-free silver thiosulfate ion complex, and ii) an amine capable of stabilizing said complex. In one embodiment, said composition is hydrophilic. In one embodiment, said composition has antimicrobial activity. In another embodiment, said antimicrobial activity is selected from the group consisting of antibacterial, antiviral and antifungal. In one embodiment, said medical device is selected from the group consisting of medical implants, a wound care device, body cavity and personal protection devices. In another embodiment, said medical device is selected from the group consisting of sutures and prosthetic implants.

Another aspect of the present invention contemplates a composition comprising an anhydrous polymer matrix, wherein said matrix comprises: i) a carrier-free silver thiosulfate ion complex and ii) an amine capable of stabilizing said complex. In one embodiment, In one embodiment, said amine is selected from the group consisting of primary, secondary and tertiary. In another embodiment, said amine comprises tri-hydroxymethyl aminomethane. In one embodiment said composition further comprises an agent selected from the group consisting of a glycerol, methanol, ethanol, propanol, butanol and polyvinylalcohol.

Another aspect of the present invention contemplates a method, comprising: a) providing; i) a catheter; and ii) a composition comprising an anhydrous polymer matrix, said matrix comprising a carrier-free silver thiosulfate ion complex and an amine capable of stabilizing said complex; and b) at least partially coating said catheter with said composition. In one embodiment, said catheter is a urinary catheter. In another embodiment, said catheter is a male exterior urine catheter.

DEFINITIONS

To facilitate understanding of the invention set forth in the disclosure that follows, a number of terms are defined below.

As used herein, the term "topically" means application to the surface of the skin, mucosa, viscera, etc.

As used herein, the term "topically active drugs" indicates a substance or composition which elicits a pharmacologic response at the site of application but which is not necessarily an antimicrobial agent.

As used herein, the term "systemically active drugs" is used broadly to indicate a substance or composition which will produce a pharmacologic response at a site remote from the point of application.

As used herein, the term "medical devices" includes any material or device that is used on, in, or through a patient's body in the course of medical treatment for a disease or injury. Medical devices include, but are not limited to, such items as medical implants, wound care devices, drug delivery devices, and body cavity and personal protection devices. The medical implants include, but are not limited to, urinary catheters, intravascular catheters, dialysis shunts, wound drain tubes, skin sutures, vascular grafts, implantable meshes, intraocular devices, heart valves, and the like. Wound care devices include, but are not limited to, general wound dressings, biologic graft materials, tape closures and dressings, and surgical incise drapes. Drug delivery devices include, but are not limited to, drug delivery skin patches, drug delivery mucosal patches and medical sponges. Body cavity and personal protection devices, include, but are not limited to, tampons, sponges, surgical and examination gloves, and toothbrushes. Birth control devices include, but are not limited to, IUD's and IUD strings, diaphragms and condoms.

As used herein, the term "silver thiosulfate ion complex", refers to silver-containing materials obtained by adding a silver halide to an aqueous solution and then adding a thiosulfate salt to the solution. Preferably, the silver complexes of the present invention are derived from the complexation of silver cations from silver halides (preferably silver chloride) with anions from the sodium thiosulfate salt. In one embodiment, the molar ratio of the thiosulfate anions to the silver cations is preferably at least 1:1 and more preferably at least 1.3:1. It is desirable that the silver thiosulfate ion complexes are solid and essentially pure, i.e., they do not contain significant amounts of waste salts or other substances that interfere with their antimicrobial activity; in addition, they do not require carrier particles. In particular, the term "silver thiosulfate ion complexes" refers to the silver-containing material produced by a process disclosed in U.S. Pat. No. 6,093,414 to Capelli. (herein incorporated by reference)

As used herein, the term "stabilized" refers to any silver thiosulfate complex that, when redissolved in an aqueous solution containing sodium chloride (i.e., for example, a wound environment), is more resistant to degradation then silver thiosulfate complexes made without a stabilizing agent (i.e., for example, an amine).

As used herein, the term "amine-stabilized" silver thiosulfate ion complex refers to any compound containing a primary, secondary or tertiary amine that, when in association with a silver thiosulfate ion complex prevents the appearance of marked degradation for at least 19 hours in an aqueous solution at 50° C. An "amine" is any nitrogen atom comprising at least one substituent.

As used herein, the term "preservative agent" refers to any compound that prolongs the ability of an amine compound to prevent the appearance of marked degradation.

As used herein, the term "marked degradation" refers to the appearance of a significant amount of black precipitation in a solution containing a silver ion complex.

As used herein, the term "impregnated" refers to any interaction between a medical device and a silver thiosulfate complex contemplated by this invention. Impregnation may be reversible or irreversible. Such impregnation may be, but is not limited to, covalent bonding, ionic bonding, Van de Waal forces or friction, and the like. A compound is impregnated to a medical device if it is attached, coated, in suspension with, in solution with, mixed with, etc.

As used herein, the term "wound" denotes a bodily injury with disruption of the normal integrity of tissue structures. In one sense the term is intended to encompass the term "surgical site". In another sense, the term is intended to encompass the terms "sore", "lesion", "necrosis" and "ulcer" which may be used interchangeably. Normally, the term "sore" is a popular term for almost any lesion of the skin or mucous membranes and the term "ulcer" is a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions. Examples of wounds which can be prevented and/or treated in accordance with the present invention are, but not limited to, aseptic wounds, contused wounds, incised wounds, lacerated wounds, non-penetrating wounds (i.e., wounds in which there is no disruption of the skin but there is injury to underlying structures), open wounds, penetrating wound, perforating wounds, puncture wounds, septic wounds, subcutaneous wounds, etc. Examples of sores are, but not limited to, bed sores, canker sores, chrome sores, cold sores, pressure sores etc. Examples of ulcers are, but not limited to, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous clear, symptomatic ulcer, trophic ulcer, tropical ulcer, venereal ulcer, e.g. caused by gonorrhoea (including urethritis, endocervicitis and proctitis). Conditions related to wounds or sores which may be successfully treated according to the invention are burns, anthrax, tetanus, gas gangrene, scarlatina, erysipelas, sycosis barbae, folliculitis, impetigo contagiosa, or impetigo bullosa, etc.

As used herein, the term "hydrophilic polymer" refers to any molecule comprising multiple subunits that is miscible in an aqueous solution.

As used herein, the term "infection" refers to any microbial invasion of living tissue that is deleterious to the organism. Microbial infections may be caused by microorganisms including, but not limited to, bacteria, viruses and fungi.

As used herein, the term "solvent" refers to any material that is capable of mixing with another solution to extract specific compounds. For example, an amine and a solvent may be added to an aqueous solution, followed by the separation of an immiscible bilayer.

As used herein, the term "matrix" refers to any combination of materials that results in a solid or semisolid structure.

DETAILED DESCRIPTION OF THE INVENTION

The present invention relates to silver ion compositions and processes for making such compositions effective as antibacterial, antiviral and/or antifungal agents. In one embodiment, the invention relates to a method of producing silver thiosulfate ion compositions, coating medical devices comprising such compositions. In a preferred embodiment, the present invention relates to carrier-free aqueous silver thiosulfate complexes stabilized by amines.

The present invention also relates to amine stabilized silver thiosulfate ion complexes that have improved water stability (i.e., maintaining antimicrobial activity in an aqueous environment). More particularly, the present invention describes amine stabilized silver thiosulfate ion complexes comprising a silver thiosulfate ion complex and an amine stabilizing agent, wherein said stabilized silver-ion complex composition is carrier-free and has increased stability when dissolved in an aqueous solution. Still further, the present invention describes amine stabilized silver thiosulfate ion complexes comprising a silver thiosulfate ion complex and an amine stabilizing agent and a preservative for said amine stabilizing agent. These compositions are useful to produce medicinals that have antibacterial, antiviral and/or antifungal activity. In one embodiment, amine stabilized silver thiosulfate ion complexes can be used to produce medical devices, such as, but not limited to, a wound dressing, an ostomy appliance, an incontinence device, and the like.

The antiseptic activity of silver compounds is a known property. Although it is not necessary to understand the mechanism of an invention, it is believed that the bacteriostatic and fungistatic effect of the silver thiosulfate complexes contemplated by the present invention is caused by the silver ion. For example, one compound known in the art that has been clinically useful is silver nitrate. Aqueous silver nitrate solutions of 0.5%–1% show disinfectant properties and are used for preventing infections in burns or for prophylaxis of neonatal conjunctivitis. Another silver compound, silver sulfadiazine, has an pronounced antibacterial effect. It is known in the art that the inherent antibacterial property of sulfadiazine ion is enhanced by complexation with a silver ion. In contrast to silver nitrate, the solubility of silver sulfadiazine is low, and hence, both the silver ion and sulfadiazine ion are present in low concentrations but may be present over a longer period of time. Silver sulfadiazine is extensively used in the treatment of wounds, in particular burns, under the trademarks Silvadene® and Flamazine®. Silver-protein combinations are yet other antiseptic formulations which have been used in low concentrations as eye drops.

Bacteriostatic silver ion compositions are marketed in various medical devices. One example is a wound dressing having an activated charcoal cloth dressing (Actisorb®, Johnson & Johnson). Another example is a wound dressing of modified pigskin impregnated with a soluble silver compound intended for treatment of burns (EZ-Derm®, Genetic Laboratories).

A specific advantage in using the silver ion as bacteriostatic agent is the general lack of formation of bacterial tolerance or resistance to the compound. This is in contrast to many types of antibiotics (i.e., development of "antibiotic resistance"). A major drawback of using ionic silver for bacteriostatic purposes is the marked degradation (i.e., appearance of a dark stain) of the silver ion complex. It is believed that this marked degradation is mediated by a chemical reduction of the silver ion to free silver. Such staining has been reported to give potentially permanent pigmentation of the skin, the so-called argyria. It is commonly recognized that silver containing compounds will also discolor under the influence of light and or heat. Additionally, radiation sterilization protocols may lead to silver ion composition color changes, irrespective of its use as a solution, cream, gel or on a medical device. These phenomena result in the avoidance of silver ion complexes by those skilled in the art when contemplating medical device sterilization. Furthermore, such medical or cosmetic products often comprise antibacterial compositions wherein discoloration is highly undesirable or unacceptable to the user.

Recently, the principles of antimicrobial photostable metal-based compositions have been disclosed. Capelli, U.S. Pat. No. 5,326,567, Oka, U.S. Pat. No. 5,429,819; and Nishino, U.S. Pat. No. 5,510,109 (all incorporated herein by reference). Specifically, the '567 patent discloses a unique "host-guest" relationship between silver ions and acyclic polyethers accomplished through the use of excess of halide ions. Additionally, the '819 patent describes a porous particulate carrier requirement for photostable compositions comprising a complexation of silver ion with a thiosulfate salt. More recently, a photostable composition comprising a complex of silver ion with a thiosulfate salt has been disclosed that does not require a porous particulate carrier.

Capelli, U.S. Pat. No. 6,093,414 (hereby incorporated by reference). The silver compositions of the '414 patent are unusually stable in the presence of both heat and light. However, in the presence of water, or any aqueous solution containing bases or polymers, even a silver thiosulfate ion complex undergoes marked degradation. Although it is not necessary to understand the mechanisms involved for successful use of the invention, it is believed that this silver thiosulfate ion complex degradation occurs because the thiosulfate ligand component of the silver thiosulfate ion complex experiences a chemical breakdown. The effect of this chemical process results in an overall destabilization and degradation of the silver thiosulfate ion complexes with concomitant loss of medicinal activity.

Amine Stabilization of Silver Ions

The improvement of silver ion composition stability in an aqueous environment is known by the formation of a complex with a primary, secondary or tertiary amine. Pedersen, U.S. Pat. No. 6,468,521 (herein incorporated by reference). Although the '521 patent discloses that the production of these amine stabilized silver complexes utilize " . . . readily soluble salts like the nitrate, lactate, or acetate or more heavily soluble salts like the halogenides such as the chloride or bromide.", there is no teaching regarding the stability of the amine stabilized silver complexes in an aqueous environment particularly wherein the aqueous environment contains a significant amount of sodium chloride. In fact, the silver ion complexes, as taught by the '521 patent, are unstable in the presence of sodium chloride ions (e.g., ions derived from dissolved sodium chloride). That is to say, in aqueous solutions containing chloride ions, the silver in the silver ion complex immediately precipitates as silver chloride. Silver chloride retains a minimal amount of antimicrobial activity due to the low dissociation rate of silver ions from silver chloride. However, the antimicrobial activity of silver chloride is poor relative to soluble silver salts or silver ion complexes.

The stability of silver ion complexes in an environment containing sodium chloride is relevant because of the importance of silver ion complexes in clinical medicine. Bodily fluids found in a typical wound environment contain a substantial amount of chloride ions. As a result, the silver ion complex compositions contemplated by the '521 patent will precipitate in the form of silver chloride when used in a wound environment. As a result, this type of silver composition has minimal in situ antimicrobial activity.

In one embodiment, the present invention contemplates a stabilized silver ion composition having antibacterial, antiviral and/or antifungal activity comprising an amine stabilized silver thiosulfate ion complex wherein said stabilizing amine is selected from the group consisting of a primary amine, a secondary amine and a tertiary amine. Preferably, stabilizing amines contemplated by various embodiments of the present invention are lower alkyl amines or amino alcohols having a free lone pair of electrons. In one embodiment, a lower alkyl stabilizing amine is selected from the group comprising mono-, di- or trimethyl, ethyl, propyl or butyl amines or mixtures thereof. In another embodiment, a lower alkyl stabilizing amino alcohol is selected from the group comprising mono-, di- or trimethyl ethyl or propyl aminoalcohols or mixtures thereof. In one embodiment, a stabilizing amine is trihydroxymethyl-aminomethane (THAM).

Amine Stabilization of Silver Thiosulfate Complexes

Specifically, silver thiosulfate ion complexes contemplated by this invention are obtained by adding a silver halide, e.g., silver chloride, to an aqueous solution and then adding a thiosulfate salt (e.g., for example, sodium thiosulfate) to the solution. Preferably, a silver thiosulfate ion complex of the present invention is derived from the complexation of a silver cation from a silver halide (e.g., for example, silver chloride) with an anion from a sodium thiosulfate salt; the molar ratio of thiosulfate anions to silver cations is preferably at least 1:1 and more preferably at least 3:1. It is desirable that silver thiosulfate ion complexes are solid and essentially pure (i.e., they do not contain significant amounts of waste salts or other substances that interfere with their antimicrobial activity) and, in addition, they do not require carrier particles (i.e., carrier-free). Though the benefit provided by the complexes of the present invention is not limited by an understanding of the precise nature of the complexes, the chemical formula of a silver thiosulfate ion complex formed when a large excess of thiosulfate salt is used is believed represented by $[Ag(S_2O_3)_3]^{5-}$. By comparison, the chemical formula of a silver thiosulfate ion complex formed when only a small excess of thiosulfate salt is used is believed represented by $[Ag_2(S_2O_3)_3]^{4-}$. In one embodiment, the present invention contemplates a silver thiosulfate ion complex represented by $[Ag_2(S_2O_3)_3]^{4-}$. Preferably, any silver thiosulfate ion complex contemplated by the present invention is a relatively pure solid form, stable, highly water soluble and antimicrobially active.

In one embodiment, the present invention contemplates an amine stabilization of aqueous carrier-free silver thiosulfate complexes, wherein amines are in molar excess of the silver thiosulfate ion complex. Preferably, amines are in 1 to 10 molar excess of the silver thiosulfate ion complex; more preferably, amines are in 2 to 5 molar excess of the silver thiosulfate ion complex.

Without restricting the invention to any specific theory, it is believed that the stabilization of a silver thiosulfate ion complex is to be ascribed to by an ionic relationship between a silver thiosulfate ion and an amine. Furthermore, it is believed that amines provide a free lone pair of electrons to establish this ionic relationship.

One of the surprising and unexpected findings of the present invention is that amine stabilized silver thiosulfate ion complexes not only have good stability in the presence of chloride ions, but such compositions have improved resistance to degradation in an aqueous environment relative to non-stabilized silver thiosulfate ion complexes as disclosed in the '414 patent. Despite the known fact that silver thiosulfate-ion compositions of '414 patent are stable against heat and light, they degrade over time in an aqueous environment. This degradation of silver thiosulfate occurs when a thiosulfate ion component of the silver thiosulfate ion complexes undergoes a chemical breakdown. The effect of this chemical process is a breakdown of silver thiosulfate ion complexes and a concomitant loss in antimicrobial activity.

While an understanding of the mechanisms involved in the successful use of the invention is not necessary, it is believed that a thiosulfate ion within a silver thiosulfate ion complex is formed by adding a sulfur atom to a sulfite ion in a complex reaction that can be summarized by the following chemical equation: $S+SO_3^{2-}=S_2O_3^{2-}$. The sulfur atom that is added to the sulfite ion to give $S_2O_3^{2-}$ is somewhat labile; thus, $S_2O_3^{2-}$ is more appropriately represented as $S-SO_3^{2-}$. Therefore, in aqueous solutions, thiosulfate decomposes over time. At moderately low pH levels the sulfur atom readily splits off, nominally yielding sulfur and sulfuric acid as follows: $S-SO_3^{2-}+H^+=S+HSO_3^{1-}$.

As a result of this inherent instability of thiosulfate ion, aqueous silver thiosulfate ion complex solutions chemically decompose over time. Although it is not necessary to understand the mechanisms of an invention, it is believed that when thiosulfate ions of the silver thiosulfate ion complex chemically break down, silver ions are released which react with simultaneously released sulfur ions to form silver sulfide. Silver sulfide is a black material having a molecular formula of $Ag_2S$. Due to silver sulfide's high dissociation constant (pK=49.1), a silver sulfide is essentially devoid of any antimicrobial activity. That is to say, silver ion is bound so tightly to the sulfur ion that minimal ionization of a silver sulfide occurs. As a result, silver sulfide provides little, if any, ionized silver to provide antimicrobial activity.

Likewise, non-stabilized silver thiosulfate ion complexes (i.e., for example, those disclosed by the '414 patent), when added to either an ointment base which contains a small proportion of water or a water-containing cream base, will decompose over a relatively short period of time with a concomitant loss of antimicrobial activity. During this degradation, the silver thiosulfate composition turns black as silver thiosulfate ion complexes decompose to silver sulfide.

In one embodiment, the present invention contemplates an improvement of the characteristic insolubility of non-stabilized silver thiosulfate complexes in non-aqueous solvents. Preferably, amine stabilized silver thiosulfate complexes are added to products such as alcohol-based mouthwashes or alcohol-based skin cleaners/washes.

In another embodiment, the compositions of the present invention are added to medical devices comprising ionic and/or polar hydrophilic polymers. Such combinations create medical devices that are effectively antimicrobial in nature, and very desirable from a practical standpoint. Preferably, hydrophilic polymers suitable for the present invention are selected from synthetic hydrophilic polymers and derivatives of animal or vegetable hydrophilic polymers. In one embodiment, a hydrophilic polymer is selected from compounds such as, but not limited to, polysaccharides (i.e., for example, cellulose derivatives such as, but not limited to, sodium carboxymethylcellulose and hydroxyethylcellulose), alginates (i.e., for example, sodium alginate), collagen (i.e., for example, porcine collagen), etc. Other preferred polymers include, but are not limited to, polylactic acid, polyhydroxybutyrates or similar polyesters, polyvinyl alcohol, polyvinylpropylene, polyacrylates, hydrophilic polyurethanes, polymaleic acid and polymers of natural origin like glucosaminoglycans, collagen and fibrin or the like, as well as copolymers or derivatives thereof. The hydrophilic polymers listed above may be crosslinked, partially crosslinked or non-crosslinked.

One aspect of the present invention contemplates compositions comprising a wound dressing and an amine stabilized silver thiosulfate ion complex. In one embodiment, a wound dressing includes, but is not limited to, gauzes and compresses, hydrocolloid dressings, xerogel dressings and foam dressings. Preferably, wound dressings comprise silver thiosulfate ion complexes according to the present invention that are readily incorporated by dissolution in water and is impregnated into said dressings or they may be introduced as an independent component of a dressing, (e.g., for example, as an adhesive composition), by any manner that is well known in the art. In one embodiment, the present invention contemplates a method for incorporating an amine stabilized silver thiosulfate ion complex into alginate fiber dressings or other similar dressings. In one embodiment, an amine stabilized silver thiosulfate ion complex is added to a solution comprising alginate prior to production of the dressing. In another embodiment, an amine stabilized silver thiosulfate ion complex is added to a solution in the form of a powder obtained by grinding a lyophilized or spray-dried silver ion composition material. In another embodiment, an amine stabilized silver thiosulfate ion complex is added to a wound dressing, wherein said stabilized complex is impregnated into an adhesive for fixing the dressing to the wound site, or into another part of the dressing, for instance onto a foam pad.

The amine stabilized silver thiosulfate ion complexes of the present invention and formulations thereof are useful for their antibacterial, antiviral and/or antifungal activity in either human or veterinary medicine. One aspect of the present invention contemplates impregnating medical devices with amine stabilized silver thiosulfate ion complexes, wherein said medical devices include, but are not limited to, medical implants, wound care devices, body cavity and personal protection devices, and the like. By way of illustration only, with no intention to limit the invention, an amine stabilized silver thiosulfate ion complex may be mixed with an anhydrous polymer matrix for coating a urinary catheter in order to prevent an infection. In another embodiment, an amine stabilized silver thiosulfate ion complex may be used in cosmetics and personal care products to provide microbial resistance. Preferably, such cosmetics may include, but are not limited to, lipsticks and glosses, lip pencils, mascaras, eye liners, eye shadows, moisturizers, liquid and powder makeup foundations, powder and cream blushes, perfumes, colognes, various creams and toners, etc., and assorted applicators like combs, brushes, sponges, and cotton swabs and balls, and examples of personal care products include deodorants, razors, shaving creams, shampoos, conditioners, various hair treatments like mousses and sprays, toothpastes, mouthwashes, dental flosses and tapes, sunscreens, moisturizers, tampons, sanitary napkins, panty shields, diapers, baby wipes, facial tissues, toilet tissues, etc.

In one embodiment, amine stabilized silver thiosulfate ion complexes are incorporated into a foam pad or related insert for uses including, but not limited to, continence care, condoms, male external urine catheters, skin adhesives etc. In another embodiment, amine stabilized silver thiosulfate ion complexes are incorporated into powders for removal of odor in incontinence pads or for incorporation into ostomy pouches. Preferably, said powders are impregnated into a medical device and are not in direct contact with the body.

One aspect of the present invention contemplates amine stabilized silver thiosulfate ion complexes impregnated into implants, sutures or other similar materials that contact body surfaces for an extended period of time; for example, during or after surgery where the risk of infection is always latent. In one embodiment, an amine stabilized silver thiosulfate ion complex is combined with a systemic prophylactic antibiotic treatment and a skin antiseptic treatment. In another embodiment, an amine stabilized silver thiosulfate ion complex is combined with antiseptics and/or antibiotics that are impregnated into a medical device intended for implantation or use within a surgical opening. Specific advantages of the present invention over previously disclosed silver ion compositions are broad spectrum antiseptic properties and long-term stability.

One aspect of the present invention contemplates impregnating or coating a medical device with a composition comprising an amine stabilized silver thiosulfate ion complex wherein said amine may be primary, secondary or tertiary and said complex is associated with one or more hydrophilic polymers. In one embodiment, the present invention contemplates a method for producing compositions having antibacterial, antiviral and/or antifungal activity wherein a silver thiosulfate ion complex is dissolved in water, an amine is added in molar excess, and the resulting solution is incubated for a period of from approximately 1 to 100 hours, preferable from approximately 12–24 hours. Optionally, after adjusting the pH using an acid to approximately 6.5–9.0, the resulting mixture is added to a hydrophilic polymer (i.e., such as, carboxymethylcellulose, hydroxyethylcellulose and alginate) and optionally dried and micronised. In another embodiment, the present invention contemplates an amine stabilized silver ion complex comprising a silver thiosulfate ion that is further associated with a primary, secondary or tertiary amine. Preferably, this amine stabilized silver thiosulfate ion complex is associated with one or more hydrophilic polymers, wherein said composition has antibacterial, antiviral and/or antifungal activity. In one embodiment, the amine stabilized silver thiosulfate complex is impregnated into a medical device including, but not limited to, a wound dressing, an ostomy appliance, an incontinence device, and other medical devices or hydrophilic coatings.

The invention is explained more in detail in the working examples below disclosing embodiments and properties of compositions of the invention. It is evident that many variations may be made without diverging from the invention the scope of which is set forth in the appended claims.

EXPERIMENTAL

In the disclosure which follows, the following abbreviations apply: L (liters); ml (milliliters); μl (microliters); g (grams); mg (milligrams); μg (micrograms); mol (moles); mmol (millimoles); μmol (micromoles); cm (centimeters); mm (millimeters); nm (nanometers); ° C. (degrees Centigrade); MW and M.W. (molecular weight); N (normal); w/w (weight-to-weight); w/v (weight-to-volume); min. (minutes); Aldrich (Milwaukee, Wis.); Columbus (Columbus Chemical Industries; Columbus, Wis.); No. (number); CFU (colony forming units); PEG (polyethylene glycol); MHM (Mueller Hinton Medium); ZOI (zone of inhibition).

EXAMPLE 1

Process for Making Silver Thiosulfate Ion Complex Compounds

This example illustrates the process for producing silver thiosulfate ion complex compounds useful for compositions of this invention.

The silver thiosulfate ion complexes were produced by first making a silver chloride precipitate in an aqueous deionized water solution (hereafter, "silver chloride precipitate/aqueous solution"). The silver chloride precipitate/aqueous solution was made by mixing 20 ml of 1 mmol/ml silver nitrate (Aldrich) with 22 ml of a 1 mmol/ml sodium chloride solution (Aldrich) in a 500 ml separatory funnel. To the resulting silver chloride precipitate/aqueous solution was added 60 ml of a 1 mmol/ml sodium thiosulfate (Columbus). The resulting mixture was agitated by shaking the separatory funnel until all of the silver chloride precipitate was dissolved.

The silver thiosulfate ion complexes produced in the above aqueous solution were separated by adding 200 ml of ethyl alcohol to the separatory funnel. Upon addition of the ethyl alcohol, the solution became cloudy and separated into two phases. The two phases were separated using the separatory funnel. The weight of the material in the phase containing the silver thiosulfate ion complexes was approximately 17 g. This phase was then treated by adding 70 ml ethyl alcohol and 40 ml of acetone to make the silver thiosulfate ion complexes essentially anhydrous. After sitting overnight, the silver thiosulfate ion complexes were in the form of a pure, white solid material in the bottom of the container. Thereafter, the solvent was decanted and the white solid was dried in an oven (62° C.) and ground to a fine white powder using a mortar and pestle. The weight of the dried silver thiosulfate ion complexes was 10.03 g.

EXAMPLE 2

Control Solution A: Silver Nitrate Solution

Silver nitrate in the amount of 0.294 mmol (50 mg) was dissolved in 10 ml of distilled water. The solution was clear and colorless.

EXAMPLE 3

Control Solution B: Silver Thiosulfate Ion-Complex Solution

A silver thiosulfate ion complex solution was made by dissolving 0.294 mmol (0.160 g) of silver thiosulfate ion complex (nominal M.W. of 537) from Example 1 into 10 ml of distilled water. The resulting solution was clear and colorless.

EXAMPLE 4

Control Solution C: Silver Nitrate—THAM Solution

A silver nitrate-THAM complex solution was made using methods described in U.S. Pat. No. 6,468,521 To Pedersen (herein incorporated by reference). Silver nitrate in the amount of 0.294 mmol (50 mg) was dissolved in 10 ml of distilled water. Tri-hydroxymethyl-aminomethane (THAM) (M.W. of 121) in the amount 2.94 mmol (0.355 g) was added to the silver nitrate solution. The silver nitrate-THAM complex was equilibrated overnight at ambient temperature. The resulting solution was clear and colorless.

EXAMPLE 5

Test Solution: Silver Thiosulfate—THAM Solution

This example describes the production of a THAM stabilized silver thiosulfate ion complex solution according to the present invention.

Silver thiosulfate powder from Example 1 in the amount 0.294 mmol (0.160 g) was dissolved in 10 ml of distilled water. Tri-hydroxymethyl-aminomethane (THAM) (M.W. of 121) in the amount 2.94 mmol (0.355 g) was added to the silver thiosulfate solution. The THAM-silver thiosulfate solution was equilibrated overnight at ambient temperature. The resulting solution was clear and colorless.

EXAMPLE 6

Stability in the Presence of Sodium Chloride

This example demonstrates that silver is an excellent antimicrobial and may be used medically to provide wound environments with antimicrobial protection.

Wound environments typically contain sodium chloride in concentrations of 0.9% (normal saline). To test stability, the solutions described in Examples 2, 3, 4 and 5 were placed in a sodium chloride environment. The stability test was performed by diluting 0.5 ml of each of the above solutions in 5 ml of normal saline (i.e., 0.9% sodium chloride in distilled water). The results of the study are shown in Table 1 below.

TABLE 1

Stability of Silver Solutions

| Sample | Distill Water | Saline |
|---|---|---|
| Control Solution A Silver Nitrate Solution (Example 2) | Clear | Precipitate |
| Control Solution B Silver Thiosulfate Solution (Example 3) | Clear | Clear |
| Control Solution C Silver Nitrate-THAM Solution (Example 4) | Clear | Precipitate |
| Test Solution Silver Thiosulfate-THAM Solution Example 5 | Clear | Clear |

The results clearly show that the solutions comprising silver thiosulfate ion complexes are more stable than solutions comprising traditional silver nitrate solution. This is especially striking when observing that THAM did not stabilize the silver nitrate solution of Example 4.

EXAMPLE 7

Resistance to Degradation in an Aqueous Environment

This example demonstrates the surprising observation that THAM-stabilized silver thiosulfate ion complexes of the present invention have improved resistance to degradation in an aqueous environments when compared to simple silver thiosulfate ion complexes.

Three vials each containing 1 ml of THAM-stabilized silver thiosulfate solution (Example 5) and three vials each containing 1 ml of non-stabilized silver thiosulfate solution (i.e., Control Solution B; Example 3) were incubated at 50° C. The samples were checked periodically for the appearance of "marked degradation". Marked degradation, as used herein, means that a solution has significant black precipitation. The results of the study identifying the time for appearance of marked degradation is as follows:

TABLE 2

Resistance to Degradation in an Aqueous Environment

| Sample | Time to Marked Degradation (Hours) |
|---|---|
| Control Solution B Silver Thiosulfate Solution Example 3 (n = 3) | <19 hours |
| Test Solution Silver Thiosulfate-THAM Solution Example 5 (n = 3) | No Marked Degradation after 36 hours |

These results clearly show that THAM-stabilized silver thiosulfate complexes have much greater stability in an aqueous environment than non-stabilized silver thiosulfate complexes.

EXAMPLE 8

Non-Aqueous Solvent Miscibility

Silver thiosulfate ion complex is very soluble in water and insoluble in most other solvents. Aqueous solubility is beneficial during the production of pure silver thiosulfate ion complex powder. However, it is advantageous to use silver thiosulfate in solutions containing non-aqueous solvents. These include products such as alcohol based mouthwashes or alcohol-based skin cleaners/washes. This example shows that THAM-stabilized silver thiosulfate ion complexes are more soluble in non-aqueous solvents than are non-stabilized silver thiosulfate ion complexes.

Nominally, 1 ml of each solution was titrated against an acetone/water solution (Lemon Nail Polish Remover; Target Corporation) and an isopropyl alcohol/methyl ethyl ketone/water solution (0.63/0.1/0.27) ("Isopropyl Solution"). The amount of solvent needed prior to the solution turning cloudy (i.e., precipitation) is used an indicator of solubility.

TABLE 3

Solvent Miscibility

| Sample | Acetone Solution | Isopropyl Solution |
|---|---|---|
| Control Solution B Silver Thiosulfate Solution (Example 3) | <2 cc (cloudy) | <2 cc (cloudy) |
| Test Solution Silver Thiosulfate-THAM Solution (Example 5) | >8 cc (remains clear) | >8 cc (remains clear) |

These data clearly show that THAM-stabilized silver thiosulfate complexes are at least 4 times more miscible in non-aqueous solutions than are non-stabilized silver thiosulfate solutions.

I claim:

1. A composition, comprising a silver thiosulfate ion complex in association with an amine, wherein said amine comprises tri-hydroxymethyl aminomethane.

2. A medical device, wherein said medical device is impregnated with a silver thiosulfate ion complex in association with an amine.

3. The device of claim 2, wherein said medical device is configured for placement inside a patient.

4. The device of claim 3, wherein said medical device is selected from the group consisting of implants, sutures and other materials left in a body cavity for a period of time.

5. The device of claim 3, wherein said medical device is a catheter.

6. The device of claim 5, wherein said catheter is a urinary catheter.

7. The device of claim 2, wherein said medical device is selected from the group consisting of an ostomy appliance and incontinent device.

8. A method, comprising:
   a) providing a patient in need of treatment using a medical device of claim 2; and
   b) treating said patient with said device.

9. A composition, comprising a silver thiosulfate ion complex in association with an amine, wherein said composition is attached to one or more hydrophilic polymers.

10. The composition of claim 9, wherein said one or more hydrophilic polymers are part of a wound dressing.

11. The composition of claim 10, wherein said wound dressing is selected from the group consisting of gauzes, compresses, hydrocolloids, xerogels and foams.

12. A method, comprising:
   a) providing;
      i) a patient exhibiting symptoms of infection; and
      ii) a composition, comprising a silver thiosulfate ion complex in association with an amine; and b) administering said composition to said patient under conditions such that at least one symptom of said infection is reduced.

13. The method of claim 12, wherein said amine is selected from the group consisting of primary amines, secondary amines and tertiary amines.

14. The method of claim 12, wherein said composition is attached to one or more hydrophilic polymers.

15. The method of claim 14, wherein said one or more hydrophilic polymers are part of a wound dressing.

16. The method of claim 15, wherein said wound dressing is selected from the group consisting of gauzes, compresses, hydrocolloids, xerogels an foams.

17. A method, comprising:
a) providing:
   i) a patient with a wound; and
   ii) a composition, comprising a silver thiosulfate ion complex in association with an amine; and
b) delivering said composition to said wound.

18. The method of claim 17, wherein said composition further comprises said amine selected from the group consisting of primary amines, secondary amines and tertiary amines.

19. The method of claim 17, wherein said composition is attached to one or more hydrophilic polymers.

20. The method of claim 19, wherein said one or more hydrophilic polymers are part of a wound dressing.

21. The method of claim 20, wherein said wound dressing is selected from the group consisting of gauzes, compresses, hydrocolloids, xerogels an foams.

22. A method, comprising:
a) providing;
   i) a patient at risk for an infection; and
   ii) a composition, comprising a silver thiosulfate ion complex in association with an amine; and
b) administering said composition to said patient.

23. The composition of claim 22, wherein said composition further comprises said amine selected from the group consisting of primary amines, secondary amines and tertiary amines.

24. The composition of claim 22, wherein said composition is attached to one or more hydrophilic polymers.

25. The composition of claim 24, wherein said one or more hydrophilic polymers are part of a wound dressing.

26. The composition of claim 25, wherein said wound dressing is selected from the group consisting of gauzes, compresses, hydrocolloids, xerogels and foams.

* * * * *